United States Patent
Marsh et al.

(10) Patent No.: US 9,119,779 B2
(45) Date of Patent: Sep. 1, 2015

(54) LOTIONED WIPE PRODUCT COMPRISING AN ANTI-STICK AGENT AND A PERFORMANCE ENHANCING AGENT

(75) Inventors: Randall Glenn Marsh, Hamilton, OH (US); Philip Andrew Sawin, Cincinnati, OH (US); Randall Alan Watson, Loveland, OH (US); Andrea Dannenberg, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 616 days.

(21) Appl. No.: 11/807,139

(22) Filed: May 25, 2007

(65) Prior Publication Data

US 2007/0286893 A1    Dec. 13, 2007

Related U.S. Application Data

(60) Provisional application No. 60/812,780, filed on Jun. 12, 2006, provisional application No. 60/855,427, filed on Oct. 31, 2006.

(51) Int. Cl.
| | |
|---|---|
| *A61K 8/55* | (2006.01) |
| *A61K 8/02* | (2006.01) |
| *A61K 8/73* | (2006.01) |
| *A61K 8/34* | (2006.01) |
| *A61K 8/39* | (2006.01) |
| *A61K 8/60* | (2006.01) |
| *A61Q 19/10* | (2006.01) |

(52) U.S. Cl.
CPC ............... *A61K 8/0208* (2013.01); *A61K 8/34* (2013.01); *A61K 8/345* (2013.01); *A61K 8/39* (2013.01); *A61K 8/55* (2013.01); *A61K 8/60* (2013.01); *A61Q 19/10* (2013.01)

(58) Field of Classification Search
CPC ......... A61K 8/55; A61K 8/0208; A61K 8/34; A61K 8/345; A61K 8/39
See application file for complete search history.

(56) References Cited

U.S. PATENT DOCUMENTS

| | | |
|---|---|---|
| 3,265,188 A | 8/1966 | Gresham |
| 3,967,756 A | 7/1976 | Barish |
| 3,982,659 A | 9/1976 | Ross |
| 3,986,479 A | 10/1976 | Bonk |
| 3,994,417 A | 11/1976 | Boedecker |
| 4,470,881 A | 9/1984 | Berg |
| 4,613,447 A | 9/1986 | Hara et al. |
| 4,840,270 A | 6/1989 | Caputo et al. |
| 4,971,220 A | 11/1990 | Kaufman et al. |
| 5,050,737 A | 9/1991 | Joslyn et al. |
| 5,143,679 A | 9/1992 | Weber et al. |
| 5,322,178 A | 6/1994 | Foos |
| 5,366,104 A | 11/1994 | Armstrong |
| 5,518,801 A | 5/1996 | Chappell et al. |
| 5,628,097 A | 5/1997 | Benson et al. |
| 5,647,506 A | 7/1997 | Julius |
| 5,648,083 A * | 7/1997 | Blieszner et al. ............. 424/402 |
| 5,658,639 A | 8/1997 | Curro et al. |
| 5,756,112 A | 5/1998 | Mackey |
| 5,785,179 A | 7/1998 | Buczwinski et al. |
| 5,791,465 A | 8/1998 | Niki et al. |
| 5,914,084 A | 6/1999 | Benson et al. |
| 5,916,661 A | 6/1999 | Benson et al. |
| D414,637 S | 10/1999 | Amundson et al. |
| D416,794 S | 11/1999 | Cormack |
| D421,901 S | 3/2000 | Hill |
| D421,902 S | 3/2000 | Hill |
| 6,083,854 A | 7/2000 | Bogdanski et al. |
| 6,092,690 A | 7/2000 | Bitowft et al. |
| 6,114,263 A | 9/2000 | Benson et al. |
| 6,129,801 A | 10/2000 | Benson et al. |
| D437,686 S | 2/2001 | Balzar et al. |
| D443,451 S | 6/2001 | Buck et al. |
| D443,508 S | 6/2001 | Braaten et al. |
| D445,329 S | 7/2001 | Zethoff |
| 6,269,969 B1 | 8/2001 | Huang et al. |
| 6,269,970 B1 | 8/2001 | Huang et al. |
| 6,296,144 B1 | 10/2001 | Tanaka et al. |
| 6,315,114 B1 | 11/2001 | Keck et al. |
| D451,279 S | 12/2001 | Chin |
| 6,383,431 B1 | 5/2002 | Dobrin et al. |
| 6,401,968 B1 | 6/2002 | Huang et al. |
| 6,412,634 B1 | 7/2002 | Telesca et al. |
| 6,440,437 B1 | 8/2002 | Krzysik et al. |
| 6,673,358 B1 * | 1/2004 | Cole et al. .................... 424/404 |
| 6,696,070 B2 | 2/2004 | Dunn |
| 6,987,195 B2 * | 1/2006 | Pereira et al. ................. 554/227 |
| 7,494,944 B2 * | 2/2009 | Talingting-Pabalan et al. ............................ 442/118 |
| 2002/0064323 A1 | 5/2002 | Chin |
| 2003/0028165 A1 | 2/2003 | Curro et al. |
| 2004/0131820 A1 | 7/2004 | Turner et al. |

(Continued)

FOREIGN PATENT DOCUMENTS

| | | | |
|---|---|---|---|
| EP | 1 694 741 A1 | | 8/2006 |
| GB | 8521484 | * | 8/1985 |

(Continued)

OTHER PUBLICATIONS

Stabylen 30 product information (3V Sigma).*

(Continued)

*Primary Examiner* — Abigail Fisher
*Assistant Examiner* — Jessica Kassa
(74) *Attorney, Agent, or Firm* — Kathleen Y. Carter

(57) ABSTRACT

An anti-stick agent and a performance enhancing agent that may be incorporated into an aqueous medium to assist in the prevention of soils and bodily exudates adhering to the skin. A substrate may be utilized to assist in delivering the anti-stick agent and the performance enhancing agent to the skin.

8 Claims, 2 Drawing Sheets

(56) References Cited

U.S. PATENT DOCUMENTS

| | | |
|---|---|---|
| 2004/0242097 A1 | 12/2004 | Hasenoehrl et al. |
| 2004/0265534 A1 | 12/2004 | Curro et al. |
| 2005/0008681 A1* | 1/2005 | Deckner et al. ............... 424/443 |
| 2005/0031568 A1* | 2/2005 | Deckner ................... 424/70.17 |
| 2005/0058833 A1 | 3/2005 | Krzysik et al. |
| 2005/0186167 A1 | 8/2005 | Ueda et al. |
| 2005/0244480 A1 | 11/2005 | Koenig et al. |
| 2009/0088360 A1* | 4/2009 | Wenzel et al. ................ 510/159 |

FOREIGN PATENT DOCUMENTS

| | | |
|---|---|---|
| JP | H5-194180 A | 8/1993 |
| JP | H9-104858 A | 4/1997 |
| JP | H10-195775 A | 7/1998 |
| JP | H11-263707 A | 9/1999 |
| JP | 2000-143478 A | 5/2000 |
| JP | 2001-270819 A | 10/2001 |
| JP | 2003-261419 | 9/2003 |
| JP | 2004-18847 A | 1/2004 |
| JP | 2004-300123 | 10/2004 |
| JP | 2005-145872 A | 6/2005 |
| JP | 2005-343943 | 12/2005 |
| WO | WO-99/55213 A1 | 11/1999 |
| WO | WO-00/27268 A1 | 5/2000 |
| WO | WO 02/42556 A | 5/2000 |
| WO | WO 00/57843 A | 10/2000 |
| WO | WO-02/14172 A1 | 2/2002 |
| WO | WO 02/100231 A | 12/2002 |
| WO | WO-2004054522 * 7/2004 ............... A61K 7/02 |
| WO | WO 2005/110354 A | 11/2005 |

OTHER PUBLICATIONS

International Search Report.

* cited by examiner

LOTIONED WIPE PRODUCT COMPRISING AN ANTI-STICK AGENT AND A PERFORMANCE ENHANCING AGENT

CROSS-REFERENCE TO RELATED APPLICATIONS

This application claims the benefit of U.S. Provisional Application No. 60/812,780 filed on Jun. 12, 2006 and U.S. Provisional Application No. 60/855,427 filed on Oct. 31, 2006 and which are incorporated herein by reference.

FIELD OF THE INVENTION

A lotioned wipe product comprising a substrate and a lotion in contact with the substrate, the lotion comprising an anti-stick agent and a performance enhancing agent may be used for delivering an improved body cleansing performance. The lotion may help reduce adhesion of soils or exudates to the skin.

BACKGROUND OF THE INVENTION

Cleaning the skin is a personal hygiene problem not always easily solved. Dry tissue products are the most commonly used cleansing products post-defecation, post-urination and during menstruation. Dry tissue products are also commonly used to remove soils, such as food and dirt, from the skin. Dry tissue products, such as those commonly used, are generally referred to as "toilet paper," "toilet tissue," or "paper towels." In addition to the use of dry tissue products, it is becoming increasingly frequent to use moistened substrates, such as wet wipes, for the purpose of cleansing the face and body after soiling, and the anus, the genital area, the perinea, and the peri-anal area after the voiding of bodily exudates. So called "wet wipes" are generally a fibrous structure impregnated with a water or oil-based lotion.

For the purpose of the present document, the anus, the perinea, the perineal area and the vulvar area are all terms indicating the body area of the pelvis between, around and including the anus and the external genitalia.

Both the perineal area and the vulvar area are marked by the presence of fine folds/wrinkles (sulci) and hair follicles, both of which make these regions more difficult anatomical areas to cleanse. During defecation, fecal matter is excreted through the anus and tends to accumulate in hard to reach locations such as around the base of hairs and in the sulci of the skin's surface. During menstruation, menses may accumulate on the skin and hair after the use of a sanitary napkin. As the fecal or menstrual matter dehydrates upon exposure to air or upon contact with an absorbent implement such as tissue paper, diaper, or sanitary napkin, it adheres more tenaciously to the skin and hair. Subsequent removal of the remaining dehydrated exudates may be even more difficult and may result in inadequate cleansing. Among those negatives associated with the failure of adequate cleansing are irritation, redness, desquamation, infections, unpleasant odor, or other kinds of personal discomfort or health related issues.

People suffering from pathological conditions (such as hemorrhoids, fissures, cryptitis, etc.) are even more susceptible to the negatives listed above. Common hygienic concerns make the benefits of a good cleansing after defecation, menstruation, and urination very relevant to babies, toddlers, children and adults. Cleansing must be efficient in terms of removal of residues and gentle in terms of absence of irritation caused by the cleansing. Wet-wipes bring a response to that basic need.

In comparison to dry tissue products, wet wipes have several benefits including:
- The enabling of a better lubrication during the use of the wipe, thereby reducing the abrasiveness of the cleansing operation;
- The hydration of the residues, thus enhancing their removal from the skin or hair;
- The hydration of the skin tissue; and
- The ability to deliver a soothing or protective lotion to the skin that can remain on the skin after the cleansing operation.

Manufacturers of wet wipes have tried to develop wipes products that deliver the right balance between normally antagonistic concepts such as:
- Enhancing the removal of soil while protecting the skin from irritation and abrasion.
- The long lasting feeling of comfortable cleanliness while avoiding a greasy feeling on the skin.

There still remains a need not only for a wet wipe that cleans effectively but that also simultaneously reduces or prevents the adhesion of soils or exudates to the skin. Such a wipe would greatly facilitate cleansing. The facilitation of cleansing by such a wipe may be reflected by a reduced deposition of soils or exudates on the skin from subsequent insults. As a result, there may be a reduction in the amount of soils or exudates on the skin at the time of the next cleaning, easier removal of the soils or exudates from the skin resulting in less abrasive damage, reduced smearing of the soils or exudates on the skin, and/or improved capture/retention of the soils or exudates on a substrate, such as a wet wipe, or within an absorbent article. The net result may be that the time and effort required by the individual to achieve a satisfactory state of cleanliness may be minimized.

There exists a further need for a wet wipe that substantially reduces or prevents adhesion of soils or exudates to the skin in a manner that is transparent to the individual using the wipe, i.e. does not require a change in habit such as the use of a separate wipe or leave an undesirable greasy layer on the skin surface.

SUMMARY OF THE INVENTION

A lotioned wipe product comprising a substrate and a lotion in contact with the substrate, the lotion comprising an anti-stick agent and a performance enhancing agent. The lotion may be effective at leaving less than about 10% w/w residual soils or exudates as measured by the Anti-Stick Screening Method. The anti-stick agent may be present at a concentration of equal to or less than about 50% w/w of the lotion composition. The performance enhancing agent may be present at a concentration of equal to or less than about 3% w/w of the lotion composition. The anti-stick agent may be water soluble.

The anti-stick agent may be selected from the group consisting of non-polymeric anti-stick agents, polymeric anti-stick agents, alkoxylated polyols, and combinations thereof. The performance enhancing agent may be selected from the group consisting of film formers, deposition aids, rheology modifiers and combinations thereof.

The lotion may further comprise an emollient and a surfactant.

An article of commerce may comprise a container housing a lotioned wipe product.

A method of preventing the adherence of soils or exudates to the skin may comprise a step of contacting the lotioned wipe product to the skin.

DETAILED DESCRIPTION OF THE INVENTION

Figure 1:
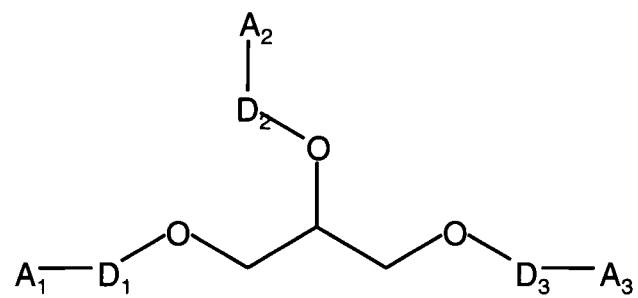
FIG. 1 is an example of the general structure to which a tris-alkoxylated glycerol may conform.

The ease with which soils and bodily exudates are removed from the skin may be related to the strength of the adhesive interactions between the soils or exudates and the skin surface. A reduction in the adhesion of the soils or exudates to the skin may enable an easier removal of the soils or exudates. A variety of materials (hereinafter referred to as anti-stick agents) have been identified that may reduce the strength of adhesion of soils or exudates to the skin. Additional materials (hereinafter referred to as "performance enhancing agents") have been identified that may improve the efficacy of the anti-stick agents, enabling the use of the anti-stick agents at a lower w/w concentration in a lotion composition. A substrate in contact with a lotion comprising an anti-stick agent and a performance enhancing agent may reduce the strength of adhesion of soils or exudates to the skin. Such a combination of a substrate and lotion may be a lotioned wipe product.

As defined herein, "weight/weight" or "w/w" refers to the weight of the component being referenced versus the weight of the total material in reference. Therefore, the use of "w/w" in substrates refers to the weight of the individual substrate component versus the weight of the total substrate. The use of "w/w" in lotions refers to the weight of the individual lotion component versus the total weight of the lotion. The use of "w/w" in water solubility refers to the weight of the material versus the weight of the total water into which the material is dissolved. The use of "w/w" for residual artificial bowel movement (ABM) refers to the weight of the remaining artificial bowel movement on the skin versus the total weight of the artificial bowel movement applied to the skin.

Substrate

A lotion may be in contact or associated with a substrate for use in the cleaning and removal of soils or exudates. "Substrate" is the general term to describe a piece of material, generally non-woven material, used in cleansing body parts. In particular, many currently available substrates may be intended for the cleansing of the perianal area after defecation. Other substrates may be available for the cleansing of the face or other body parts.

The substrate may be a nonwoven material. "Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coform, or other such processes known in the art for such purposes. The nonwoven structure may comprise one or more layers of such fibrous assemblies, wherein each layer may include continuous fibers, coextruded fibers, non-continuous fibers and combinations thereof.

The fibers of the substrate may be any natural, cellulosic, and/or wholly synthetic material. Examples of natural fibers may include cellulosic natural fibers, such as fibers from hardwood sources, softwood sources, or other non-wood plants. The natural fibers may comprise cellulose, starch and combinations thereof. Non-limiting examples of suitable cellulosic natural fibers include, but are not limited to, wood pulp, typical northern softwood Kraft, typical southern softwood Kraft, typical CTMP, typical deinked, corn pulp, acacia, eucalyptus, aspen, reed pulp, birch, maple, radiata pine and combinations thereof. Other sources of natural fibers from plants include, but are not limited to, albardine, esparto, wheat, rice, corn, sugar cane, papyrus, jute, reed, sabia, raphia, bamboo, sidal, kenaf, abaca, sunn, rayon (also known as viscose), lyocell, cotton, hemp, flax, ramie and combinations thereof. Yet other natural fibers may include fibers from other natural non-plant sources, such as, down, feathers, silk, cotton and combinations thereof. The natural fibers may be treated or otherwise modified mechanically or chemically to provide desired characteristics or may be in a form that is generally similar to the form in which they can be found in nature. Mechanical and/or chemical manipulation of natural fibers does not exclude them from what are considered natural fibers with respect to the development described herein.

The synthetic fibers can be any material, such as, but not limited to, those selected from the group consisting of polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof. Further, the synthetic fibers can be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. It is also possible to use bicomponent fibers. These bicomponent fibers can be used as a component fiber of the structure, and/or they may be present to act as a binder for the other fibers present in the fibrous structure. Any or all of the synthetic fibers may be treated before, during, or after manufacture to change any desired properties of the fibers.

In certain embodiments, it may be desirable to have particular combinations of fibers to provide desired characteristics. For example, it may be desirable to have fibers of certain lengths, widths, coarseness or other characteristics combined in certain layers or separate from each other. The fibers may be of virtually any size and may have an average length from about 1 mm to about 60 mm. Average fiber length refers to the length of the individual fibers if straightened out. The fibers may have an average fiber width of greater than about 5 micrometers. The fibers may have an average fiber width of from about 5 micrometers to about 50 micrometers. The fibers may have a coarseness of greater than about 5 mg/100 m. The fibers may have a coarseness of from about 5 mg/100 m to about 75 mg/100 m.

Additionally, it may be desirable for the fibers to have certain compositional characteristics. For example, in the instance where the lotion may comprise hydrophilic (i.e. water soluble) ingredients that ultimately are intended to be imparted to the skin during cleansing, it may be desirable that the fibers comprise hydrophobic materials to reduce the tendency of the hydrophilic ingredients to adhere to the fibers, thereby reducing their availability to the skin. Without being bound by theory, it is believed that the lotion ingredients may partition between the lotion and the fibers during storage and between the lotion and the fibers and the skin during cleansing. In the instance where the lotion comprises a hydrophilic ingredient that is to be imparted to the skin during cleansing, the use of hydrophobic fibers in the substrate favors the partitioning, and subsequent delivery, of the hydrophilic ingredient to the skin.

Hydrophobic fibers can be any material, such as, but not limited to, those selected from the group consisting of polyesters (e.g., polyethylene terephthalate), polyolefins, polypropylenes, polyethylenes, polyethers, polyamides, polyesteramides, and combinations thereof. Further, the hydrophobic fibers can be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof.

The fibers may be circular in cross-section, dog-bone shape, delta (i.e., triangular cross section), trilobal, ribbon, or other shapes typically produced as staple fibers. Likewise, the fibers can be conjugate fibers such as bicomponent fibers. The fibers may be crimped and may have a finish, such as a lubricant, applied.

The substrate materials may also be treated to improve the softness and texture thereof. The substrate may be subjected to various treatments, such as, but not limited to, physical treatment, such as hydro-molding, hydro-embossing, ring rolling, as described in U.S. Pat. No. 5,143,679 issued to Weber et al. on Sep. 1, 1992; structural elongation, as described in U.S. Pat. No. 5,518,801 issued to Chappell et al. on May 21, 1996; consolidation, as described in U.S. Pat. No. 5,914,084 issued to Benson et al. on Jun. 22, 1999; U.S. Pat. No. 6,114,263 issued to Benson et al. on Sep. 5, 2000; U.S. Pat. No. 6,129,801 issued to Benson et al. on Oct. 10, 2000 and U.S. Pat. No. 6,383,431 issued to Dobrin et al. on May 7, 2002; stretch aperturing, as described in U.S. Pat. No. 5,628,097 issued to Benson et al. on May 13, 1997; U.S. Pat. No. 5,658,639 issued to Curro et al. on Aug. 19, 1997 and U.S. Pat. No. 5,916,661 issued to Benson et al. on Jun. 29, 1999; differential elongation, as described in US Publication No. 2003/0028165A1 published on Feb. 6, 2003 by Curro et al.; and other solid state formation technologies as described in U.S. Publication No. 2004/0131820A1 published on Jul. 8, 2004 by Turner et al. and U.S. Publication No. 2004/0265534A1 published on Dec. 30, 2004 by Curro et al., zone activation, and the like; chemical treatment, such as, but not limited to, rendering part or all of the substrate hydrophobic, and/or hydrophilic, and the like; thermal treatment, such as, but not limited to, thermal-embossing, softening of fibers by heating, thermal bonding and the like; and combinations thereof.

Without being bound by theory, it is believed that a textured substrate may further enable the ease of removal of the bodily exudates by improving the ability to grip or otherwise lift the exudates from the skin during cleansing. Any one of a number of texture elements may be useful in improving the ability to grip or otherwise lift the exudates from the skin during cleansing such as, but not limited to continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, etc. and combinations thereof. The texture elements may be hollow elements. The texture elements may be connected to each other. The texture elements may overlap each other.

The substrate may have a basis weight between about 15, 30, 40 or 45 grams/m$^2$ and about 65, 75, 85, 95 or 100 grams/m$^2$. A suitable substrate may be a carded nonwoven comprising a 40/60 blend of viscose fibers and polypropylene fibers having a basis weight of 58 grams/m$^2$ as available from Suominen of Tampere, Finland as FIBRELLA™ 3160. FIBRELLA™ 3160 is a 58 grams/m$^2$ nonwoven web comprising 60% w/w 1.5 denier polypropylene fibers and 40% w/w 1.5 denier viscose fibers. Another suitable material may be FIBRELLA™ 3100 which is a 62 grams/m$^2$ nonwoven web comprising 50% w/w 1.5 denier polypropylene fibers and 50% w/w 1.5 denier viscose fibers. In both of these commercially available fibrous webs, the average fiber length is about 38 mm. Another suitable material for use as a substrate may be SAWATEX™ 2642 as available from Sandler AG of Schwarzenbach/Salle, Germany. Yet another suitable material for use as a substrate may have a basis weight of from about 50 grams/m$^2$ to about 60 grams/m$^2$ and have a 20/80 blend of viscose fibers and polypropylene fibers. The substrate may also be a 60/40 blend of pulp and viscose fibers.

In one embodiment, the surface of the substrate may be essentially flat. In another embodiment, the surface of the substrate may optionally contain raised and/or lowered portions. These can be in the form of logos, indicia, trademarks, geometric patterns, images of the surfaces that the substrate is intended to clean (i.e., infant's body, face, etc.). They may be randomly arranged on the surface of the substrate or be in a repetitive pattern of some form.

In another embodiment, the substrate may be biodegradable. For example the substrate could be made from a biodegradable material such as a polyesteramide, or a high wet strength cellulose.

Lotion

"Lotion," as used herein, refers to a composition comprising a carrier such as water. The lotion further comprises an anti-stick agent and a performance enhancing agent. Additional optional ingredients may be added to the lotion as desired, as described herein, to form a lotion composition. The lotion may form a film on the surface of the skin and may provide increased repellency of residual soils or exudates at a low level of anti-stick agent.

Performance Enhancing Agent

Performance enhancing agents, as defined herein, refer to materials that enhance the deposition, wettability, tenacity, uniformity, stability, or combinations thereof, of a film that may be formed on the skin surface after treatment with either an anti-stick agent alone or a lotion comprising an anti-stick agent.

Without being bound by theory, it is believed that performance enhancing agents may enhance the efficacy of anti-stick agents or lotions comprising anti-stick agents and thereby enable lower w/w concentrations of anti-stick agents to be used. It is surmised this may occur by enabling the anti-stick agent or the lotion to spread more easily over the skin surface to form a film, by enhancing the adherence of the anti-stick agent or lotion to the skin surface to render it more durable or resistant to wash-off or rub-off, by enabling the anti-stick agent or lotion to wet the skin surface more effectively, by enabling the film that is formed to be more uniform, by enabling the film that is formed to be more resistant to rupture, or combinations thereof.

Performance enhancing agents may include, but are not limited to, materials that may generally be known as film formers, deposition aids, rheology modifiers, or combinations thereof.

Film formers may include, but are not limited to, polyvinylpyrolidone, hydroxypropylcellulose, ethylcellulose, methylhydroxypropylcellulose, methyl ethyl cellulose, copolymer condensates comprising ethylene oxide and propylene oxide, and polyethylene glycol. Other suitable film formers are gums, such as agar, guar gum, gum arabic, gum arabic uses, gum ghatti, gum karaya, hydroxypropyl guar gum, and xanthan gum; alginates, such as calcium alginate and calcium-sodium alginate; protein film formers such as pectin, albumen, poly amino acids (e.g. polylysine), and gelatin; and waxes such as carnauba wax. Combinations of the above may also be used.

Rheology modifiers are compounds that may impact the way in which other materials or compositions deform and flow. Rheology modifiers may increase the viscosity of the lotion composition, may provide "structure" to the lotion composition, may help to stabilize the lotion composition on a substrate, may enhance the transfer of the lotion composition to the skin surface, and may enhance the uniformity of the film of the lotion composition on the skin.

Rheology modifiers may also affect the rheological profile of the lotion composition such that the viscosity of the lotion composition may change as a function of the shear that is applied to the lotion composition. The application of the lotion composition to a surface (e.g. the skin) typically includes a "wiping" or "rubbing" movement. This movement may increase the shear and pressure experienced by the lotion composition. In the case of a shear-thinning rheological profile (i.e. an increase in shear reduces the viscosity of the lotion composition), the viscosity of the lotion may decrease with the increased shear of "wiping" or "rubbing" thereby enabling a better transfer to the skin as well as a better lubrication effect.

Non-limiting examples of rheology modifiers include, but are not limited to, rheology modifiers comprising:
  polysaccharide units, e.g. cellulose, xanthan gum, diutan gum, carrageenan, gellan gum, welan gum, pectin, sclerotium gum, starch, galactoarabinan, alginate, and modified-forms thereof;
  homopolymers of acrylic acid;
  acrylic acid cross-linked with a polyfunctional compound, e.g. carbomer and acrylate crosspolymer;
  copolymers of acrylic acid, acrylate esters, maleic acid and the like, generally known as the alkali swellable emulsions (ASE) group;
  hydrophobically-modified copolymers of acrylic acid, acrylate esters, maleic acid and the like, generally known as the hydrophobically-modified alkali swellable emulsions (HASE) group;
  polyethylene glycol units of varying length connected by urethane linkages and terminated with hydrophobic end groups, generally known as the hydrophobically-modified ethoxylated urethane resins (HEUR) group; and
  combinations thereof.

In an embodiment, the rheology modifier may be Keltrol™, as available from CP Kelco, San Diego, Calif. In an embodiment, the rheology modifier may be Ticaxan™, as available from TIC Gums, Belcamp, Md. In an embodiment, the rheology modifier may be Rhodicare™ D, as available from Rhodia, Cranbury, N.J. Additional examples of rheology modifiers include, but are not limited to, Ultrez™-10, a carbomer and Pemulen™ TR-2, an acrylate crosspolymer, both of which are available from Noveon, Cleveland Ohio.

Performance enhancing agents may be used at a weight/weight % (w/w) from about 0.05%, 0.1%, 0.15%, 0.18%, 0.2%, 0.3%, 0.4%, or 0.5% to about 1%, 2%, or 3%.

It is to be noted that some film formers, deposition aids, and rheology modifiers can have multiple functions, e.g. a rheology modifier may enhance both deposition and film formation.

While particular performance enhancing agents have been illustrated and described, it would be obvious to those skilled in the art that various other performance enhancing agents may be used without departing from the spirit and scope of the invention.

Anti-Stick Agent

As used herein, the term "anti-stick agent" refers to water-soluble materials which may help reduce or prevent the adherence of soils or exudates to bodily surfaces, thereby facilitating subsequent cleanings. "Soils" refers herein to material from a source extraneous to the body, such as dirt and food. "Exudates" refers herein to material from a source internal to the body, such as urine, menses, feces, and mucus.

Without being bound by theory, it is believed that anti-stick agents may reduce the adhesive force between the soils or exudates and the skin surface such that the adhesive forces may be smaller than the cohesive forces within the soils or exudates, thereby allowing the soils or exudates to detach from the skin surface upon application of a shear force such as that generated by wiping. It is not intended that this mechanism describe the means by which all anti-stick agents described herein function. Other possible mechanisms of reducing adhesion to skin will be obvious to those skilled in the art.

The use of non-water soluble materials to reduce adhesion of soils or exudates to skin is known in the art. Materials such as silicones, mineral oil, petrolatum, plant-derived oils, and other hydrophobic emollients are known in wet wipes in the form of emulsions. Examples of such emulsions may be found in U.S. Pat. No. 6,083,854 issued Jul. 4, 2000 to Bogdanski et al; U.S. Pat. No. 5,648,083 issued Jul. 15, 1997 to Blieszner et al.; and U.S. Pat. No. 6,440,437 issued Aug. 27, 2002 to Krzysik et al.

While non-water soluble materials such as those described above may deliver some level of anti-stick performance, they suffer from several major setbacks including:
  they often leave an undesirable greasy or slippery feel on the skin, and
  they are typically lubricious, reducing interaction of the cleansing implement and the soils or exudates, resulting in smearing and poor cleaning.

Water soluble anti-stick agents overcome many of these setbacks. For the purposes of the present invention, an anti-stick agent is considered water soluble if about 0.01%, 0.1%, 0.5%, or 1.0% w/w or greater dissolves in water at 25° C. Water soluble anti-stick agents may have the following advantages:
  they typically do not leave a greasy feeling on the skin, and
  they are typically not as lubricous as non-water soluble anti-stick agents and may result in better cleaning and less smearing.

There is a further need for a substrate that may be in contact with a lotion that may deliver good repellency of soils or exudates while utilizing low concentration levels of anti-stick agent, such as less than or equal to about 10% w/w concentration of anti-stick agent in the lotion. Such a lotioned substrate may be cost effective due to the decreased amount of anti-stick agent required to deliver the benefit and due to the ease of incorporation of the anti-stick agent into the lotion due to the water solubility of the anti-stick agent. Further, the anti-stick agent may result in a cleansing benefit such as the repellency of soils or exudates and may result in no sensory negatives on the skin such as a greasy or slippery film. Consumers may prefer a substrate that can deliver an anti-stick benefit while being used for routine cleansing, i.e. consumers may not prefer an additional step to the process of cleansing, such as the use of one substrate to clean and the use of an additional substrate that cleans poorly but provides the anti-stick benefit. An example of a wipe containing a hydrophobic anti-stick agent that cleans poorly and needs to be used as a separate wipe is described in US 2005/0244480A1.

The strength of adhesion between two materials may be analyzed in a variety of methods to determine whether or not the adhesive interactions are impacted by surface treatments or other factors. Examples of adhesion tests for determining if a treatment has reduced adhesion between two materials (such as by reducing the force of adhesion to less than the force of cohesion) include ASTM D2919, ASTM D3528 and related methods referred to or described therein. Such methods may test the strength of adhesion through the application of shear.

A method for assessing the adhesion of soils or exudates to the skin surface has been detailed herein. It has been discovered that some anti-stick agents, used at a low level (e.g., in a lotion), may provide an anti-stick benefit on skin, but the magnitude of this anti-stick benefit is greatly reduced on artificial surfaces. Without being bound by theory, it is believed that factors such as the wettability, surface energy, and surface chemistry of skin are critical for the formation of effective anti-stick films containing certain water soluble anti-stick agents.

The test for assessing the adhesion of soils or exudates to the skin is described in detail in the TEST METHODS section. Briefly, the Anti-Stick Screening Method treats the skin surface with a defined amount of anti-stick agent or a lotion comprising the anti-stick agent. A defined amount of an artificial pasty bowel movement ("ABM") is applied. The ABM is covered with a square piece of paper, and compressed with a defined force for a defined amount of time. The paper is then peeled away slowly with forceps. The paper is tared before application of the ABM and is re-weighed after removal from the skin. The percent residual ABM on the skin is calculated as the weight of the artificial bowel movement (ABM) remaining on the skin versus the weight of the artificial bowel movement originally applied to the skin. The ABM, similar to real infant BM, fails cohesively, resulting in part of the ABM remaining on the skin surface and part of the ABM remaining on the piece of paper. The more efficient the anti-stick agent or lotion comprising the anti-stick agent, the less residual ABM on the skin surface. While artificial ABM is utilized in the Anti-Stick Screening Method, the artificial ABM may correlate in physical properties to soils or exudates. The percent residual artificial ABM may, therefore, be utilized as an equivalent measurement of the percent residual soils or exudates.

An anti-stick agent beneficial for use may leave less than about 10%, 8%, 7%, 5%, 4%, 3% or 2% residual soils or exudates on the skin surface as assessed by the Anti-Stick Screening Method. Skin that is not treated with an anti-stick agent, either alone or within a lotion, but is otherwise subjected to the above method may serve as a negative control. Typically, no treatment of the skin results in about 30-35% residual soils or exudates remaining on the skin surface.

Conventional substrates comprising a lotion, both aqueous-based and emulsion-based, may deliver anti-stick performance in the range of about 15-30% residual soils or exudates in the above method. It has been discovered that this level of performance is insufficient to deliver a consumer noticeable anti-stick benefit.

The lotion of the present invention may comprise at least about 0.05% w/w of an anti-stick agent and at least about 0.01% of a performance enhancing agent. The lotion may comprise equal to or less than about 50% w/w of an anti-stick agent and equal to or less than about 3% of a performance enhancing agent. The lotion may comprise an anti-stick agent at a level from about 0.05%, 0.1%, 0.5%, 1%, 2%, 4% or 5% to about 8%, 10%, 20%, 25% or 50% w/w of the lotion composition. The lotion may comprise a performance enhancing agent at a level from about 0.05%, 0.1%, 0.15%, 0.18%, 0.2%, 0.3%, 0.4%, or 0.5% to about 1%, 2%, or 3% w/w of the lotion composition.

The lotion comprising an anti-stick agent and a performance enhancing agent may be effective at leaving less than about 10% residual soils or exudates on the skin as measured by the Anti-Stick Screening Method as described herein. Such a lotion may leave less than about 2%, 3%, 4%, 5%, 7%, 8% or 10% residual soils or exudates remaining on the skin. A lotion composition comprising an anti-stick agent at a level of about 2% and a performance enhancing agent at a level of about 0.18% may leave less than about 10% residual soils or exudates on the skin. A lotion composition comprising an anti-stick agent at a level of about 2% and a performance enhancing agent at a level of about 0.18% may leave less than about 8% residual soils or exudates on the skin. A lotion composition comprising an anti-stick agent at a level of about 5% and a performance enhancing agent at a level of about 0.18% may leave less than about 4% residual soils or exudates on the skin. The lotion comprising the anti-stick agent and performance enhancing agent, as described herein, may be in contact with or associate with a substrate. The lotioned wipe product may also be effective at leaving less than about 10%, 8%, 7%, 5%, 4%, 3%, or 2% residual soils or exudates on the skin.

Water-soluble anti-stick agents include, but are not limited to:

Non-polymeric anti-stick agents such as glycerol and related polyols such as sorbitol, maltitol, xylitol, pentaerythitol, sucrose, glucose, maltose, maltotriose, maltodextrin, maltopentose, maltohexose, and isomaltulose, ethylene glycol, propylene glycol, butylene glycol, and the like, Polymeric anti-stick agents comprising polyethylene glycol, polypropylene glycol, polybutylene glycol, polyglycerol or mixtures thereof, including block copolymers comprising ethylene oxide and propylene oxide, and the like, Alkoxylated polyol compounds, Phosphate compounds such as mono-alkyl phosphates and di-alkyl phosphates, and combinations of the above.

Non-Ipolymeric Anti-Stick Agents:

Non-polymeric anti-stick agents, such as those listed above, may provide an anti-stick benefit. Non-polymeric anti-stick agents may be required at relatively high levels in the composition relative to polymeric anti-stick agents.

Polymeric Anti-Stick Agents:

Polymeric anti-stick agents comprising polyethylene glycol, polypropylene glycol, polybutylene glycol, polyglycerol or mixtures thereof, including block copolymers comprising ethylene oxide and propylene oxide, have been found to be useful as anti-stick agents. Commercially available examples of polymeric anti-stick agents include the Carbowax™ and Polyox™ series as available from The Dow Chemical Company of Midland, Mich., and the Pluronic™, Pluronic™ R, Tetronic™, and Tetronic™ R surfactant series as available from BASF Corporation of Florham Park, N.J. In one embodiment, a lotion comprising Carbowax™ 400 at a level of about 5% w/w and a performance enhancing agent at a level of about 0.18% w/w may leave less than about 9% residual soils or exudates on the skin. In another embodiment, a lotion comprising a Pluronic™, such as Pluronic™ F68, at a level of about 2% w/w and a performance enhancing agent at a level of about 0.18% w/w may leave less than about 10% residual soils or exudates on the skin. In yet another embodiment, a lotion comprising a Pluronic™, such as Pluronic™ F68, at a level of about 5% w/w and a performance enhancing agent at a level of about 0.18% w/w may leave less than about 4% residual soils or exudates on the skin.

Figure 2:
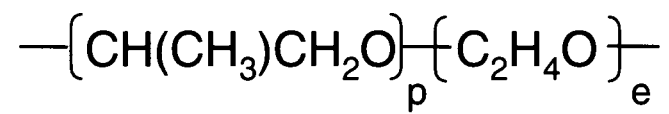
FIG. 2 is an example of the general structure to which a combination of polyoxyethylene and polyoxypropylene may conform.

Alkoxylated Polyol Compounds:

Alkoxylated polyol compounds have also been found to deliver an anti-stick benefit. The alkoxylated polyol compounds useful in the present invention comprise a central polyol moiety comprising at least three hydroxyl groups, with at least one of the hydroxyl groups being alkoxylated. The alkoxyl group comprises polyoxyethylene, polyoxypropylene, polyglycerol and/or mixtures thereof. The average total degree of alkoxylation may be from about 1 to about 100. FIG. 1 is an illustration of the general structure to which a tris-alkoxylated glycerol may conform wherein:

$A_1$, $A_2$, and $A_3$ are hydrogen, methyl, or any mixture thereof, $D_1$, $D_2$, and $D_3$ are polyoxyethylene, polyoxypropylene, or combinations thereof as illustrated in FIG. 2. In one embodiment, p may average 4.2 and e may average 13.4.

The alkoxylated polyol compounds useful in the present invention may further have at least one of the alkoxy moieties comprising at least one anionic capping group, as described in WO2005/063847. In one embodiment, $A_1$, is hydrogen, or methyl, $A_2$ and $A_3$ are sulfate ($SO_3^-$), $D_1$, $D_2$, and $D_3$ are polyoxyethylene, polyoxypropylene, or combinations thereof as illustrated in FIG. 2. In one embodiment, p may average 4.2 and e may average 13.4.

In another embodiment, a lotion may comprise a tris-alkoxylated glyceryl bis-sulfate at a level of about 2% w/w and a performance enhancing agent at a level of about 0.18% and may leave less than about 8% w/w residual soils or exudates on the skin.

It can be appreciated by one skilled in the art that any appropriate polyol compound can function as the central polyol moiety, and that any number of alkoxyl groups of one or greater, and any number of anionic capping groups can be used. It can also be appreciated that the alkoxyl groups can be of any type described, and need not be identical. It can also be appreciated that the anionic capping groups can be of any type described, and need not be identical.

Phosphate Compounds

Phosphate compounds may include mono-alkyl phosphates and di-alkyl phosphates.

Figure 3:
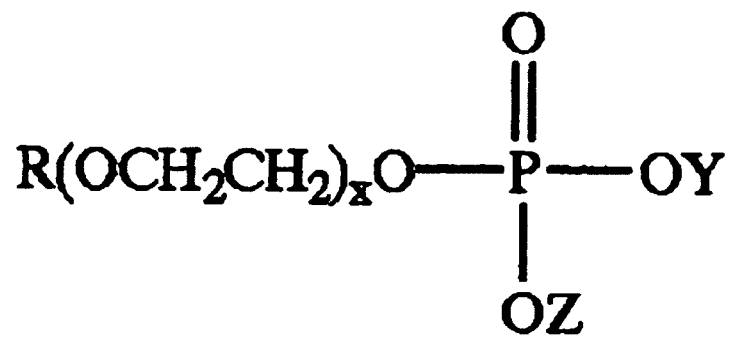
FIG. 3 is an example of the general structure of a mono alkyl phosphate.

Mono-alkyl phosphates may have the structural formula as illustrated in FIG. 3 wherein R represents a saturated or unsaturated hydrocarbon group having an average of from 8 to 22 carbon atoms, x represents a number from 0 to 20 and each of Y and Z represents hydrogen, an alkali metal, ammonium or an alkanol amine.

Figure 4:
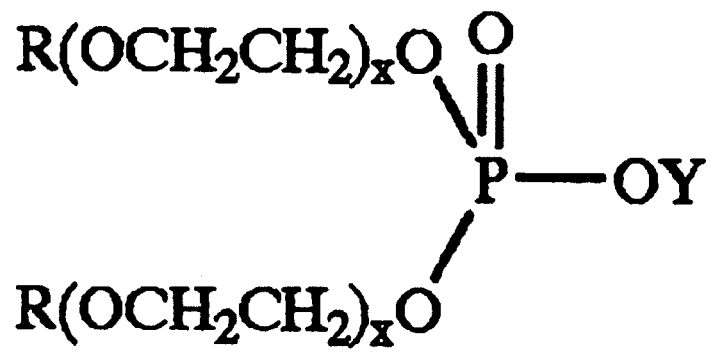
FIG. 4 is an example of the general structure of a dialkyl phosphate.

Di-alkyl phosphates may have the structural formula as illustrated in FIG. 4 wherein R represents a saturated or unsaturated hydrocarbon group having an average of from 8 to 22 carbon atoms, x represents a number from 0 to 20 and each of Y and Z represents hydrogen, an alkali metal, ammonium or an alkanol amine.

The saturated or unsaturated hydrocarbon groups having an average of from 8 to 22 carbon atoms can be straight chain, branched or alicyclic hydrocarbons as are known to those skilled in the art. In an embodiment, the saturated or unsaturated hydrocarbon groups may have an average from 10 to 18 carbon atoms.

Alkali metals and amines may include, but are not limited to, lithium, sodium, potassium, dimethylmonoethanolamine, methyldiethanolamine, trimethylamine, triethylamine, dibutylamine, butyldimethylamine, monoethanolamine, diethanolamine, triethanolamine, isopropyldimethylamine and isopropylethanolamine.

Optional Lotion Ingredients

Additional ingredients may be added to the lotion as desired to create a lotion composition. The composition may generally comprise any of the following ingredients: emollients, surfactants, preservatives, or a combination of preservative compounds acting together as a preservative system or other adjunct ingredients. It is to be noted that some ingredient compounds can have a multiple function and that all compounds are not necessarily present in the composition. The composition may be an aqueous-based solution or an emulsion. The pH of the composition may be from about pH 3, 4, or 5 to about pH 7, 7.5, or 8.

Examples of lotions and lotion compositions that may be used may be found in the Examples section as Examples 1 through 12.

Emollient

Emollients may (1) improve the glide of the substrate on the skin, by enhancing the lubrication and thus decreasing the abrasion of the skin, (2) hydrate the residues (for example, fecal residues or dried urine residues or menses), thus enhancing their removal from the skin, (3) hydrate the skin, thus reducing its dryness and irritation while improving its flexibility under the wiping movement, and (4) protect the skin from later irritation (for example, caused by the friction of an absorbent article) as the emollient is deposited onto the skin and remains at its surface as a thin protective layer.

Emollients may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

A useful mixture of emollients is caprylic capric triglycerides in combination with Bis-PEG/PPG-16/16 PEG/PPG-16/16 dimethicone known as ABIL CARE™ 85 (available from Degussa Care Specialties of Hopewell, Va.).

Emollients, when present, may be used in the present invention at a weight/weight % from about 0.5%, 1% or 4% to about 0.001%, 0.01%, or 0.02% w/w. Without being bound by theory, it is believed that low levels of emollients are desirable as this may reduce the tendency of the emollients to form a greasy or oily layer on the skin, which may not be consumer preferred.

Surfactant

The surfactant can be an individual surfactant or a mixture of surfactants. The surfactant may be a polymeric surfactant or a non-polymeric one. The surfactant may be employed as an emulsifier. The surfactant, when present, may be employed in an amount effective to emulsify the emollient and any other non-water-soluble oils that may be present in the composition, such as an amount ranging from about 0.5%, 1%, or 4% w/w to about 0.001%, 0.01% or 0.02% w/w (based on the weight surfactant over the weight of the composition).

The composition may include one or more surfactants. The surfactant or combinations of surfactants may be mild, which means that the surfactants provide sufficient cleansing or detersive benefits but do not overly dry or otherwise harm or damage the skin.

A wide variety of surfactants are useful herein and include those selected from the group consisting of anionic surfactants, nonionic surfactants, cationic surfactants, amphoteric surfactants, zwitterionic surfactants, and mixtures thereof.

A wide variety of anionic surfactants are useful herein. Non-limiting examples of anionic surfactants include those selected from the group consisting of sarcosinates, sulfates, sulfonates, isethionates, taurates, phosphates, lactylates, glutamates, and mixtures thereof. Amongst the isethionates, the alkoyl isethionates are useful, and amongst the sulfates, the alkyl and alkyl ether sulfates are useful. Other anionic materials useful herein are soaps (i.e., alkali metal or amine salts, e.g., sodium, potassium or triethanol amine salts) of fatty acids, typically having from about 8 to about 24 carbon atoms.

Nonionic surfactants useful herein include, but are not limited to, those selected from the group consisting of alkyl glucosides, alkyl polyglucosides, polyhydroxy fatty acid amides, alkoxylated fatty acid esters, alkoxylated fatty alcohol ethers, sucrose esters, amine oxides, and mixtures thereof.

Suitable amphoteric or zwitterionic surfactants for use in the compositions herein include those which are known for use in hair care or other personal care cleansing. Amphoteric surfactants suitable for use in the present compositions are well known in the art and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Useful amphoteric surfactants include, but are not limited to, the group consisting of cocoamphoacetate, cocoamphodiacetate, lauroamphoacetate, lauroamphodiacetate, and mixtures thereof.

Zwitterionic surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Useful zwitterionic detersive surfactants are the betaines, amphoacetates and sulfobetaines, e.g., cocoamidopropylbetaine, sodiumlaurylamphoacetate and cocoamidopropylhydroxysultaine.

Preservative

Controlling microbiological growth may be beneficial in water based products such as lotion compositions intended for application to substrates in forming wipes. The lotion composition may comprise a preservative or a combination of preservatives acting together as a preservative system. Preservatives and preservative systems are used interchangeably in the present document to indicate one unique or a combination of preservative compounds. A preservative may be understood to be a chemical or natural compound or a combination of compounds reducing the growth of microorganisms, thus enabling a longer shelf life for a package of substrates (opened or not opened) as well as creating an environment with reduced growth of microorganisms when transferred to the skin during the wiping process.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Materials useful as preservatives include, but are not limited to: methylol compounds, iodopropynyl compounds, simple aromatic alcohols, paraben compounds, chelators such as ethylenediamine tetraacetic acid, and combinations thereof.

In one embodiment, the preservative system may comprise a methylol compound or its equivalent, an iodopropynyl compound and mixtures thereof. Methylol compounds may release a low level of formaldehyde when in a water solution that has an effective preservative activity. Exemplary methylol compounds include, but are not limited to, diazolidinyl urea (GERMALL® II as is available from International Specialty Products of Wayne, N.J.), N-[1,3-bis(hydroxyl -methyl)-2,5-dioxo-4-imidazolidinyl]-N,N'-bis(hydroxymethyl) urea, imidurea (GERMALL® 115 as is available from International Specialty Products of Wayne, N.J.), 1,1-methylene bis[3-[3-(hydroxymethyl)-2,5-dioxo-4-imidazolidinyl] urea], 1,3-dimethylol-5,5-dimethyl hydantoin (DMDMH), sodium hydroxymethyl glycinate (SUTTOCIDE® A as is available from International Specialty Products of Wayne, N.J.), and glycine anhydride dimethylol (GADM). Methylol compounds can be used at concentrations between about 0.025% and about 0.50% w/w. In another embodiment, the concentration may be about 0.075% w/w. The iodopropynyl compound may provide antifungal activity. An exemplary material may be iodopropynyl butyl carbamate as is available from Clariant UK, Ltd. of Leeds, The United Kingdom as NIPACIDE™ IPBC. Another exemplary material may be 3-iodo-2-propynylbutylcarbamate. Iodopropynyl compounds can be used effectively at a concentration between about 0.001% and about 0.05% w/w. The concentration may be about 0.009% w/w. A preservative system of this type may comprise a blend of a methylol compound at a concentration of about 0.075% w/w and an iodopropynyl compound at a concentration of about 0.009% w/w.

In another embodiment, the preservative system may comprise simple aromatic alcohols (e.g. benzyl alcohol). Materials of this type may have effective antibacterial activity. Benzyl alcohol is available from Symrise, Inc. of Teterboro, N.J.

In another embodiment, the preservative may comprise at least one paraben antimicrobial. The preservative may be a paraben antimicrobial selected from the group consisting of methylparaben, ethylparaben, propylparaben, butylparaben, isobutylparaben or combinations thereof. The total concentration of paraben antimicrobial may be lower than about 0.3%, 0.5%, or 1% w/w. The minimum amount of paraben antimicrobial may be any amount sufficient to obtain the desired preservation of the composition, such as more than about 0.001%.

In another embodiment, acidic compounds used in sufficient amount to reduce the pH of the lotion composition (e.g. pH of less than about 5) may be useful as the preservative, or as a potentiator for other preservative ingredients.

In another embodiment, chelators, such as ethylenediamine tetraacetic acid and its salts, may also be used in preservative systems as a potentiator for other preservative ingredients.

Adjunct Ingredients

The lotion composition may optionally include other adjunct ingredients. Possible adjunct ingredients may be selected from a wide range of additional ingredients such as, but not limited to perfumes and fragrances, texturizers, colorants, soothing agents and medically active ingredients, such as healing actives and skin protectants.

Article of Commerce

In one embodiment, an article of commerce may be provided. The article of commerce may comprise a container as described herein and at least one substrate as described herein.

Containers useful may include, but are not limited to, PET tubs, flow wrap pouches, precut sachets for individually packed cleansing mitts, and other packaging known in the art as suitable for nonwoven articles. Additionally, the container may also be manufactured to facilitate removal of individual cleansing substrates.

The container may be made of any suitable material or materials and can be manufactured in any suitable manner. For example, the container can be made of polystyrene, polypropylene, PET, POET, polyethylene, polyester, polyvinyl alcohol, or the like. The containers may also be made of a mixture of the above materials. The containers may be manufactured by, for example, a vacuum molding process or an injection molding process, or any suitable process.

Additional information on containers, as well as additional optional components for containers, including, but not limited to: container bodies, lids, container features, such as, but not limited to, attachment of lids, hinges, zippers, securing aids, and the like, can be found in U.S. Pat. Nos. Des. 451,279; Des. 437,686; Des. 443,508; Des 443,451; Des 421,901; Des 421,902; Des 416,794; Des 414,637; Des 445,329; U.S. Pat. Nos. 3,982,659; 3,967,756; 3,986,479; 3,994,417; 6,269,970; 5,785,179; 5,366,104; 5,322,178; 5,050,737; 4,971,220; 6,296,144; 6,315,114; 4,840,270; 4,471,881; 5,647,506; 6,401,968; 6,269,969; 6,412,634; 5,791,465; 6,092,690; U.S. Patent Application Publication No. 2002/0064323 published on May 30, 2002, issued to Chin; and WO 00/27268 published on May 18, 2000 and assigned to The Procter & Gamble Company; WO 02/14172 published on Feb. 21, 2002 and assigned to The Procter & Gamble Company; and WO 99/55213 published on Nov. 4, 1999 and assigned to The Procter & Gamble Company.

Anti-Stick Screening Method

This method may be used for assessing the adhesion of soils or exudates to the skin by quantifying the percentage of residual artificial pasty bowel movement ("ABM") left on the skin surface after treatment. The ABM, similar to real infant BM, fails cohesively, resulting in part of the ABM remaining on the skin surface and part of the ABM being removed. The more efficient the anti-stick agent or lotion comprising the anti-stick agent and the performance enhancing agent, the lower the percentage of residual ABM on the skin surface.

At least eight healthy adults participate in a single screening study. Each of the panelists completes a four-day washout period during which they use Olay® unscented moisturizing soap, as distributed by The Procter and Gamble Company, Cincinnati, Ohio, to wash their forearms. Panelists must refrain from using any topical product, such as ointments, creams or lotions, on their forearms during this washout-out period and also on the day of the screening study. On the day of testing, panelist's arms are inspected to ensure they are free of cuts, scratches, and rashes. If any skin abnormalities are present, the panelist cannot participate.

A template and a fine-tip marker are used to mark-off up to ten 3 cm by 3 cm sites on the volar forearms, i.e. up to ten sites per panelist. All but one of these sites are treated with an anti-stick agent or a lotion comprising an anti-stick agent. The remaining site receives no anti-stick treatment, i.e. serves as a negative control. The locations of the various treatments, including the no-treatment site, may be randomized among the sites on each panelist. Testing starts at the site closest to the elbow on the left arm and, as testing on each site is completed, progresses to the site closest to the wrist on the left arm, then to the site closest to the elbow on the right arm, and finally to the site closest to the wrist on the right arm. Testing on each site requires approximately 4 minutes, for a total time per panelist of approximately 40 minutes.

For each site that is treated, 1 $\mu$l/cm$^2$ or 9 $\mu$l/site of anti-stick agent or lotion comprising an anti-stick agent and a performance enhancing agent is applied in the center of the site using a standard or positive displacement pipettor. The applied agent or lotion is then spread over the entire site (the boundary of which is defined by the marks made using the template) using a powder-free finger cot, Catalog # 56613-413 as available from VWR Scientific of West Chester, Pa., by placing the finger cot on top of the agent or lotion droplet and lightly rubbing the finger cot over the skin surface using several side-to-side and up-and-down movements for a total elapsed time of 10-15 seconds. Examining the site from an oblique angle, the person conducting the test needs to ensure that a uniform film has been formed over the entire area of the site. The film is left exposed to air, untouched, for approximately 1 minute prior to proceeding with the subsequent steps.

A 1 ml syringe, such as Catalog # BD-309628 as available from VWR Scientific of West Chester, Pa., that has been filled with room temperature ABM and is devoid of air bubbles, is placed onto a tared four-place analytical balance. The weight is recorded. The syringe with ABM is held over the center of the test site on the forearm, in reasonably close proximity to the skin surface, and approximately 0.2 ml of ABM is dispensed onto the skin by pressing the plunger and by watching the gradations on the syringe. The ABM should form a reasonably uniform, compact mound in the center of the test site. The syringe is re-weighed on the analytical balance, and the weight is recorded. The quantity of ABM that was delivered to the forearm is calculated by subtracting the second weight from the first.

A 4 cm×4 cm piece of weigh paper, Catalog # 12578-201 as available from VWR Scientific of West Chester, Pa., is tared on the four place analytical balance, centered over the ABM mound on the forearm test site, and gently lowered onto the ABM using forceps. The weigh paper must not be touched with fingertips, as this may transfer oils onto its surface. Next, a 500 g bottle-shaped weight, such as Catalog # 12766-518 as available from VWR Scientific of West Chester, Pa., that exerts approximately 0.5 psi of downward force is placed over the weigh paper such that the mound of ABM under the weigh paper is approximately centered under the weight. The weight may be gently held in place or balanced on the forearm by the panelist for 30 seconds. After 30 seconds have elapsed, two fingers are placed gently on either side of the weigh paper to hold it in place, and the 500 g weight is slowly lifted. Using a pair of forceps, the weigh paper is slowly and gently peeled from the test site. The forceps are placed at the lower right corner of the weigh paper, and the weigh paper is slowly peeled upwards in the direction of the upper left corner of the weigh paper. It should take approximately 1-2 seconds to remove the weigh paper. Once removed, the weigh paper is placed back onto the analytical balance that it was tared on, and the weight is recorded to determine the amount of ABM removed.

The above steps are repeated until all sites per panelist have been tested, i.e. the steps consisting of application of anti-stick agent or lotion comprising an anti-stick agent and a performance enhancing agent, application of ABM, application of weigh paper, application of weight, and removal of weigh paper. For the no-treatment control, application of agent or lotion is skipped and ABM is applied directly to the skin site.

An example of a spreadsheet to collect the various weight measurements and to calculate the percent (%) residual ABM left on the arm is as follows:

| Sub | Site | Trtmnt | Syringe | Syringe After | ABM Applied | ABM Removed | % ABM Arm |
|-----|------|--------|---------|---------------|-------------|-------------|-----------|
| 101 | 1 | I | 7.8561 | 7.6351 | 0.2210 | 0.1678 | 24.07 |
| 101 | 2 | J | 7.6343 | 7.4241 | 0.2102 | 0.1967 | 6.42 |
| 101 | 3 | H | 7.4223 | 7.2208 | 0.2015 | 0.1473 | 26.90 |
| 101 | 4 | A | 7.2200 | 7.0090 | 0.2110 | 0.1754 | 16.87 |
| 101 | 5 | G | 7.0080 | 6.8087 | 0.1993 | 0.1755 | 11.94 |
| 101 | 6 | B | 7.8082 | 7.5957 | 0.2125 | 0.2042 | 3.91 |
| 101 | 7 | F | 7.5943 | 7.3862 | 0.2081 | 0.1536 | 26.19 |
| 101 | 8 | C | 6.9643 | 6.7592 | 0.2051 | 0.1526 | 25.60 |
| 101 | 9 | E | 7.3840 | 7.1725 | 0.2115 | 0.1984 | 6.19 |
| 101 | 10 | D | 7.1711 | 6.9678 | 0.2033 | 0.1788 | 12.05 |

Wherein:
Sub refers to the subject number, which is minimally 101 to 108 and ideally 101 to 110, i.e. the above chart would be replicated 8 to 10 times to cover all panelists.
Site refers to arm location, starting with the left arm near the elbow (Site 1) and proceeding to the right arm near the wrist (Site 10).
Trtmnt refers to the code of the treatment applied, typically a letter from A–J.
Syringe refers to the initial weight of the syringe containing ABM.
Syringe After refers to the final weight of the syringe containing ABM once approximately 0.2 ml of ABM has been dispensed onto a treatment site.
ABM Applied is a calculated value obtained from the equation Syringe – Syringe After = ABM Applied.
ABM Removed refers to the weight of the ABM that has been captured on the tared weigh paper after the weigh paper has been peeled from a treatment site.
% ABM Arm is a calculated value obtained from the equation ((ABM Applied – ABM Removed)/ABM Applied) × 100. This is a measure of the percent (%) residual ABM on the skin surface after treatment.

The mean and standard error of the mean ("SEM") for each treatment, e.g. A-J, for all panelists, e.g. 101-110, is calculated and graphed.

When the method is run correctly, the no treatment control may yield a value between approximately 30% to 35% residual ABM.

This method may also be used to assess expressed lotion compositions from commercially available wipe products. Expressed lotion compositions are prepared by inserting the entire wipe stack of a non-expired marketed product into a pre-cleaned press capable of exerting about 80 psi downward force on the stack. Ideally, the lower plate of the press contains a channel into which the expressed lotion may collect, and a hole through which the expressed lotion may flow into a clean storage container. An example of a suitable storage container is Catalog # 83008-666 as available from VWR Scientific of West Chester, Pa. All expressed lotions are stored at room temperature prior to use.

On the day prior to the study, 10 ml of each anti-stick agent or lotion composition is transferred into a glass scintillation vial such as Catalog # 66022-060 as available from VWR Scientific of West Chester, Pa. Each vial is labeled with the treatment code, e.g. A-J. On the day of the study, the anti-stick agent or lotion composition is drawn from the scintillation vial with the standard or positive displacement pipettor and applied to the respective treatment site as described in the method. By having the various treatments in the scintillation vials, it is very easy to rearrange the vials in between panelists to accommodate the randomization scheme for the study.

To ensure reproducible results, the Anti-Stick Screening Method should be run at a room temperature of 21° C.±2° C. and at a relative humidity of 30-50%.

Preparation of Artificial Pasty Bowel Movement (ABM)
The following equipment is required:
an analytical balance accurate to ±0.001 g
a homogenizer capable of stirring the ingredients to homogeneity, such as an Ika Labortechnik™ T25 basic or equivalent as available from Ika-Werke GmbH and Co. KG of Staufen, Germany.
a homogenizer probe to be used with the homogenizer, such as Catalog # S25N 25F as available from Ika-Werke GmbH and Co. KG of Staufen, Germany.
The following reagents are required:
Feclone™ Powder #4, available from SiliClone Studio, Valley Forge, Pa., as Catalog Number Feclone BFPS-4.
Feclone™ Powder #6, available from SiliClone Studio, Valley Forge, Pa., as Catalog Number BFPS-6.
Feclone™ Powder #7, available from SiliClone Studio, Valley Forge, Pa., as Catalog Number BFPS-7.
Carbopol™ 981, available from BF Goodrich, Cleveland, Ohio.
Deionized water.
The following quantities of the above reagents are required:

| Ingredient | Grams |
|------------|-------|
| Deionized water for Carbopol ™ solution | 78.78 |
| Feclone ™ powder #4 | 6.600 |
| Feclone ™ powder #6 | 6.600 |
| Feclone ™ powder #7 | 6.600 |
| Carbopol ™ 981 | 0.900 |

The procedure to prepare the ABM consists of the following steps:
A. Preparation of Carbopol™ Solution
  1. Weigh 78.78 g±0.01 g of deionized water in a 250 ml beaker.
  2. Weigh 0.900 g±0.001 g of Carbopol™ on weigh paper.
  3. Put beaker on a magnetic stirrer and set speed at 400 rpm.
  4. Add Carbopol™ powder slowly to the water, over the span of about 5 minutes. While adding the Carbopol™, increase the stirring speed slowly to 600 rpm.
  5. Once the Carbopol™ powder has been added to the water, cover the beaker and continue mixing at 600 rpm for 15 minutes. The Carbopol™ powder must be completely dispersed, i.e. a transparent gel without any agglomerates.
  6. Set up a hot plate at 150° C. Place the Carbopol™ solution on the hot plate and continue mixing at 600 rpm until the solution is heated to 81° C. to 83° C.
B. Preparation of ABM Mixture
  1. Weigh 6.600 g±0.01 g each of Feclone powders #4, #6, and #7 into a beaker and mix well.
  2. Using a T25 basic or equivalent homogenizer with a homogenizer probe, stir the Carbopol™ solution at 8000 rpm for about 30 seconds before proceeding with Step 3.
  3. To the Carbopol™ solution that is being stirred, slowly add the Feclone™ powder mixture, about one quarter of the total at a time. Ensure that the Feclone™ powder mixture gets pulled through the homogenizer probe during addition, i.e. is thoroughly mixed into the pasty composition that is forming. If necessary, use a spatula to facilitate incorporation of the Feclone™ powder mixture into the composition.
  4. After all of the Feclone™ powder mixture has been added, continue mixing with the homogenizer at 8000 rpm for an additional 5 minutes, using the spatula to push the pasty composition towards the homogenizer probe. The composition should be thoroughly mixed and appear homogeneous.

The finished ABM may be placed in a container, such as Catalog # 14233-954 as available from VWR Scientific of West Chester, Pa., and stored in the refrigerator for up to 30 days. After 30 days, a new sample should be prepared for further experiments. The container must be tightly sealed to avoid drying out of the ABM.

Prior to using the ABM in the Anti-Stick Screening Method, the ABM must be removed from the refrigerator and allowed to adjust back to room temperature. An easy way to accomplish this is to fill a 10 ml syringe, such as Catalog # BD301604 as available from VWR Scientific of West Chester, Pa., with cold ABM and then allow the syringe to equilibrate to room temperature on a counter top. Equilibration typically takes about 15 minutes. The 10 ml syringe can then be used to fill the 1 ml syringe described in the Anti-Stick Screening Method.

EXAMPLES

The lotion compositions of Examples 1 through 12 are contacted as described earlier with a substrate such as Fibrella 3160, a 58 grams/m$^2$ nonwoven comprising a blend of 40% viscose fibers and 60% polypropylene fibers as is available from Suominen of Tampere, Finland or any other substrate deemed suitable for use.

In the Examples, "Q.S" refers herein to "quantum sufficit" and is a sufficient percentage of water added to the composition to bring the overall composition to 100%.

| Components | Weight Percent | | | |
| --- | --- | --- | --- | --- |
| | Example 1 | Example 2 | Example 3 | Example 4 |
| Water | Q.S. | Q.S. | Q.S. | Q.S. |
| Disodium EDTA | 0.100 | 0.100 | 0.100 | 0.100 |
| Iodopropynylbutylcarbamate | 0.009 | 0.009 | 0.009 | 0.009 |
| Benzyl Alcohol | 0.500 | 0.500 | 0.500 | 0.500 |
| Suttocide ® A 50% Solution | 0.150 | 0.150 | 0.150 | 0.150 |
| Xanthan Gum | 0.180 | 0.180 | 0.180 | 0.180 |
| PEG40 Hydrog. Castor Oil | 0.550 | 0.550 | 0.550 | 0.550 |
| Abil Care 85 | 0.100 | 0.100 | 0.100 | 0.100 |
| Citric Acid | 0.055 | 0.055 | 0.055 | 0.055 |
| Perfume | 0.070 | 0.070 | 0.070 | 0.070 |
| Carbowax ® 400 | 5.000 | | | |
| Pluronic ® F68 | | 2.000 | | |
| Pluronic ® F68 | | | 5.000 | |
| Tris-Alkoxylated Glyceryl Bis-Sulfate | | | | 2.000 |

| Components | Weight Percent | | | |
| --- | --- | --- | --- | --- |
| | Example 5 | Example 6 | Example 7 | Example 8 |
| Water | Q.S. | Q.S. | Q.S. | Q.S. |
| Disodium EDTA | 0.100 | 0.100 | 0.100 | 0.100 |
| PEG40 Hydrog. Castor Oil | 0.400 | 0.400 | 0.400 | 0.400 |
| Propylene Glycol | 1.500 | 1.500 | 1.500 | 1.500 |
| Phenoxyethanol | 0.800 | 0.800 | 0.800 | 0.800 |
| Methyl Paraben | 0.150 | 0.150 | 0.150 | 0.150 |
| Ethyl Paraben | 0.050 | 0.050 | 0.050 | 0.050 |
| Propyl Paraben | 0.050 | 0.050 | 0.050 | 0.050 |
| Xanthan Gum | 0.180 | 0.180 | 0.180 | 0.180 |
| Abil Care 85 | 0.100 | 0.100 | 0.100 | 0.100 |
| Trilaureth-4 Phosphate | 0.400 | 0.400 | 0.400 | 0.400 |
| Monobasic Sodium Phosphate | 0.180 | 0.180 | 0.180 | 0.180 |
| Perfume | 0.070 | 0.070 | 0.070 | 0.070 |
| Carbowax ® 400 | 5.000 | | | |
| Pluronic ® F68 | | 2.000 | | |
| Pluronic ® F68 | | | 5.000 | |
| Tris-Alkoxylated Glyceryl Bis-Sulfate | | | | 2.000 |

| Components | Weight Percent | | | |
| --- | --- | --- | --- | --- |
| | Example 9 | Example 10 | Example 11 | Example 12 |
| Water | Q.S. | Q.S. | Q.S. | Q.S. |
| Disodium EDTA | 0.100 | 0.100 | 0.100 | 0.100 |
| Xanthan Gum | 0.180 | 0.180 | 0.180 | 0.180 |
| Abil Care 85 | 0.100 | 0.100 | 0.100 | 0.100 |
| Sodium Benzoate | 0.120 | 0.120 | 0.120 | 0.120 |
| PEG40 Hydrog. Castor Oil | 0.440 | 0.440 | 0.440 | 0.440 |
| Citric Acid | 0.530 | 0.530 | 0.530 | 0.530 |
| Trisodium Citrate | 0.390 | 0.390 | 0.390 | 0.390 |
| Benzyl Alcohol | 0.300 | 0.300 | 0.300 | 0.300 |
| Perfume | 0.070 | 0.070 | 0.070 | 0.070 |
| Euxyl ® PE9010$^\Delta$ | 0.300 | 0.300 | 0.300 | 0.300 |
| Carbowax ® 400 | 5.000 | | | |
| Pluronic ® F68 | | 2.000 | | |

-continued

| | | |
|---|---|---|
| Pluronic ® F68 | 5.000 | |
| Tris-Alkoxylated Glyceryl Bis-Sulfate | | 2.000 |

<sup>A</sup>As available from Schuelke and Mayr GmbH of Norderstedt, Germany.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A lotioned wipe product comprising:
   a. a substrate;
   b. a lotion comprising a water-soluble anti-stick agent, and a performance enhancing agent wherein said lotion is in contact with said substrate; further wherein the lotion comprises between 0.05% to 5% w/w of said water-soluble anti-stick agent, said anti-stick agent comprising an alkoxylated polyol compound, wherein said alkoxylated polyol compound comprises a central polyol moiety comprising three hydroxyl groups, wherein the three hydroxyl groups are alkoxyl groups, wherein said alkoxyl groups comprise materials selected from the group consisting of polyoxyethylene, polyoxypropylene, and mixtures thereof, wherein the average total degree of alkoxylation is from about 1 to about 100, wherein said alkoxyl groups comprise a phosphate capping group, and said performance enhancing agent is xanthan gum.

2. The wipe product of claim 1 wherein said lotion is effective at leaving less than about 10% w/w residual soils or exudates as measured by the Anti-Stick Screening Method.

3. The wipe product of claim 1 wherein said substrate comprises hydrophobic fibers.

4. The wipe product of claim 1 wherein said substrate is textured.

5. The wipe product of claim 1 wherein said lotion comprises greater than 0.05% w/w of said performance enhancing agent.

6. The wipe product of claim 1 wherein said lotion comprises from about 0.05% w/w to about 3% w/w of said performance enhancing agent.

7. The wipe product of claim 1 wherein said lotion further comprises an emollient and a surfactant.

8. A method of preventing the adherence of soils or exudates to the skin comprising a step of contacting said skin with said wipe product of claim 1.

* * * * *